US00PP23655P2

(12) United States Plant Patent
Lannes

(10) Patent No.: US PP23,655 P2
(45) Date of Patent: Jun. 11, 2013

(54) ***MANDEVILLA* PLANT NAMED 'LANUTAH'**

(50) Latin Name: *Mandevilla Sanderi*
Varietal Denomination: Lanutah

(75) Inventor: Robert Lannes, Malause (FR)

(73) Assignee: D.H.M. Innovation S.A.S., Malause (FR)

( * ) Notice: Subject to any disclaimer, the term of this patent is extended or adjusted under 35 U.S.C. 154(b) by 0 days.

(21) Appl. No.: 13/374,930

(22) Filed: Jan. 23, 2012

(51) Int. Cl.
*A01H 5/00* (2006.01)

(52) U.S. Cl.
USPC ..... Plt./232

(58) Field of Classification Search
USPC ..... Plt./232
See application file for complete search history.

(56) References Cited

PUBLICATIONS

Pluto Plant Variety Database 2012-05 search for Lanutah.*

* cited by examiner

*Primary Examiner* — Annette Para
(74) *Attorney, Agent, or Firm* — C. A. Whealy

(57) ABSTRACT

A new and distinct cultivar of *Mandevilla* plant named 'Lanutah', characterized by its vining plant habit; moderately vigorous to vigorous growth habit; glossy small dark green-colored leaves; early and freely flowering habit; and dark red purple-colored flowers.

2 Drawing Sheets

Botanical designation: *Mandevilla Sanderi.*
Cultivar denomination: 'LANUTAH'.

BACKGROUND OF THE INVENTION

The present invention relates to a new and distinct cultivar of *Mandevilla* plant, botanically known as *Mandevilla Sanderi* and hereinafter referred to by the name 'Lanutah'.

The new *Mandevilla* plant is a product of a planned breeding program conducted by the Inventor in Malause, France. The objective of the breeding program is to create new vining *Mandevilla* plants with dark red purple-colored flowers.

The new *Mandevilla* plant originated from a cross-pollination conducted by the Inventor in Malause, France on Aug. 20, 2006 of a proprietary selection of *Mandevilla Sanderi* identified as code number 05-075-22, not patented, as the female, or seed parent with *Mandevilla Sanderi* 'Sunmanderemi', disclosed in U.S. Plant Pat. No. 16,449, as the male, or pollen, parent. The new *Mandevilla* plant was discovered and selected by the Inventor as a single flowering plant from within the progeny of the stated cross-pollination in a controlled greenhouse environment in Malause, France in May, 2008.

Asexual reproduction of the new *Mandevilla* plant by cuttings in a controlled greenhouse environment in Malause, France, since May, 2010 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Lanutah'. These characteristics in combination distinguish 'Lanutah' as a new and distinct *Mandevilla* plant:

1. Vining plant habit.
2. Moderately vigorous to vigorous growth habit.
3. Glossy small dark green-colored leaves.
4. Early and freely flowering habit.
5. Dark red purple-colored flowers.

Plants of the new *Mandevilla* can be compared to plants of the female parent selection. Plants of the new *Mandevilla* differ primarily from plants of the female parent selection in the following characteristics:

1. Plants of the new *Mandevilla* flower earlier than plants of the female parent selection.
2. Plants of the new *Mandevilla* have star-shaped flowers whereas plants of the female parent selection have rounded flowers.
3. Plants of the new *Mandevilla* have larger flowers than plants of the female parent selection.

Plants of the new *Mandevilla* can be compared to plants of the male parent, 'Sunmanderemi'. Plants of the new *Mandevilla* differ primarily from plants of 'Sunmanderemi' in the following characteristics:

1. Plants of the new *Mandevilla* flower earlier than plants of 'Sunmanderemi'.
2. Plants of the new *Mandevilla* have star-shaped flowers whereas plants of 'Sunmanderemi' have rounded flowers.
3. Plants of the new *Mandevilla* have larger flowers than plants of 'Sunmanderemi'.

Plants of the new *Mandevilla* can also be compared to plants of *Mandevilla Sanderi* 'Sherry', not patented. In side-by-side comparisons conducted in Malause, France, plants of the new *Mandevilla* differed from plants of 'Sherry' in the following characteristics:

1. Plants of the new *Mandevilla* were more vigorous than plants of 'Sherry'.
2. Plants of the new *Mandevilla* were more freely flowering than plants of 'Sherry'.
3. Plants of the new *Mandevilla* had larger flowers than plants of 'Sherry'.
4. Flowers of plants of the new *Mandevilla* were darker in color than flowers of plants of 'Sherry'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Lanutah' grown in a container.

The photograph on the second sheet is a close-up view of a typical flowering plant of 'Lanutah'.

DETAILED BOTANICAL DESCRIPTION

The aforementioned photographs and following observations, measurements and values describe plants grown during the autumn in two-liter containers in polyethylene-covered greenhouse in Malause, France and under cultural practices typical of *Mandevilla* commercial production. During the production of the plants, day temperatures ranged from 8° C. to 26° C. and night temperatures ranged from 3° C. to 15° C. Plants were six months old when the photographs and description were taken. In the following description, color references are made to The Royal Horticultural Society Colour Chart, 2007 Edition, except where general terms of ordinary dictionary significance are used.

Botanical classification: *Mandevilla Sanderi* 'Lanutah'.

Parentage:

*Female, or seed, parent*.—Proprietary selection of *Mandevilla Sanderi* identified as code number 05-075-22, not patented.

*Male, or pollen, parent*.—*Mandevilla Sanderi* 'Sunmanderemi', disclosed in U.S. Plant Pat. No. 16,449.

Propagation:

*Type*.—By vegetative cuttings.

*Time to initiate roots, summer*.—About two weeks at 23° C. to 25° C.

*Time to initiate roots, winter*.—About three weeks at 23° C. to 25° C.

*Time to produce a rooted young plant, summer*.—About five to six weeks at 23° C. to 25° C.

*Time to produce a rooted young plant, winter*.—About six to eight weeks at 23° C. to 25° C.

*Root description*.—Fibrous, fine; light yellowish white in color.

*Rooting habit*.—Freely branching; medium density.

Plant description:

*Plant and growth habit*.—Vining plant habit; mostly upright; moderately vigorous to vigorous growth habit.

*Plant height*.—About 59.5 cm.

*Plant diameter (spread)*.—About 43.8 cm.

*Lateral branch description*.—Branching habit: Freely branching habit with about 14 lateral branches developing per plant; pinching enhances lateral branch development. Length: About 31.2 cm. Diameter: About 2 mm. Internode length: About 2.5 cm. Strength: Strong. Texture: Smooth, glabrous. Color: Close to 143A; older stems, close to N199B.

Foliage description:

*Arrangement*.—Opposite, simple.

*Length*.—About 4.9 cm.

*Width*.—About 3.3 cm.

*Shape*.—Obovate.

*Apex*.—Abruptly acute.

*Base*.—Obtuse with truncate tendencies.

*Margin*.—Entire.

*Texture, upper and lower surfaces*.—Smooth, glabrous; glossy.

*Venation pattern*.—Pinnate, reticulate.

*Color*.—Developing leaves, upper surface: Darker than between N137A and 147A. Developing leaves, lower surface: Close to 146A strongly tinged with close to N199A. Full expanded leaves, upper surface: Darker than between N137A and 147A; venation, close to 143B. Fully expanded leaves, lower surface: Close to 147B; venation, close to 145C.

*Petiole length*.—About 1.5 cm.

*Petiole diameter*.—About 1 mm.

*Petiole texture, upper and lower surfaces*.—Smooth, glabrous.

*Petiole color, upper and lower surfaces*.—Close to 144B.

Flower description:

*Flower type and flowering habit*.—Single salverform flowers arranged in axillary racemes; flowers star-shaped and face mostly outwardly; about three flowers developing per inflorescence and about 40 flowers developing per plant.

*Natural flowering season*.—Early flowering habit with plants begin to flower about six weeks after planting; plants flower continuously from summer into the autumn in France.

*Flower longevity on the plant*.—About seven days; flowers not persistent.

*Fragrance*.—Very faint, pleasant.

*Flowers*.—Appearance: Flared trumpet, corolla fused and five-parted. Diameter: About 8.4 cm. Depth (length): About 6.9 cm. Tube length: About 5.2 cm.

*Flower buds*.—Length: About 4.2 cm. Diameter: About 7 mm. Shape: Narrowly obovate. Color: Close to 144D.

*Corolla*.—Quantity and arrangement: Five petals arranged in a single whorl and fused at the base. Petal length: About 8.9 cm. Petal width: About 3.2 cm. Petal shape and appearance: Roughly spatulate; lower 60% of the petal is fused. Petal apex: Acute. Petal margin: Entire. Petal texture, upper and lower surfaces: Smooth, glabrous; velvety. Throat texture: Smooth, glabrous. Tube texture: Smooth, glabrous. Color: Petal, when opening, upper surface: Close to 187A tinged with close to 53A; throat, close to 35A, towards the base of the throat, close to 145A. Petal, when opening, lower surface: Close to 187A to 187B slightly tinged with close to 53A; tube, close to 53A to 53C, towards the base of the tube, close to 145A tinged with close to 42C to 42D. Petal, fully opened, upper surface: Between 59A and 187B tinged with close to 53A; throat, close to 31A, towards the base of the throat, close to 145B; with development, color becoming closer to darker than 187A tinged with close to 53A. Petal, fully opened, lower surface: Between 59A and 187B; tube, close to 53B and towards the base of the tube, close to 145B.

*Corona*.—Quantity and arrangement: Five sepals arranged in a single whorl. Sepal length: About 9 mm. Sepal width: About 2 mm. Sepal shape: Lanceolate. Sepal apex: Narrowly acuminate. Sepal base: Roughly truncate. Sepal margin: Entire. Sepal texture, upper and lower surfaces: Smooth, glabrous. Sepal color: Immature, upper and lower surfaces: Close to 145B; towards the base, close to 144B. Mature, upper and lower surfaces: Close to 145B; towards the base, close to 144B.

*Peduncles*.—Length: About 8.5 cm. Diameter: About 1.5 mm. Texture: Smooth, glabrous. Strength: Flexible, but strong. Color: Close to 143A; upper side tinged with close to N199A.

*Pedicels*.—Length: About 1.5 cm. Diameter: About 1.5 mm. Texture: Smooth, glabrous. Strength: Flexible, but strong. Color: Close to 143A; upper side tinged with close to 175D.

*Reproductive organs*.—Stamens: Quantity and arrangement: Typically five; basifixed; anthers connivent. Filament length: About 1 mm. Anther shape: Ellipsoidal. Anther length: About 1 cm. Anther color: Close to 162D. Pollen amount: None observed. Pistils: Quantity: Typically one. Pistil length: About 2.4 cm. Style length: About 2.1 cm. Style color: Close to 145C. Stigma shape: Conical. Stigma color: Close to 143C. Ovary color: Close to 144C.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be hardy to USDA Hardiness Zone 9.

It is claimed:

1. A new and distinct *Mandevilla* plant named 'Lanutah' as illustrated and described.

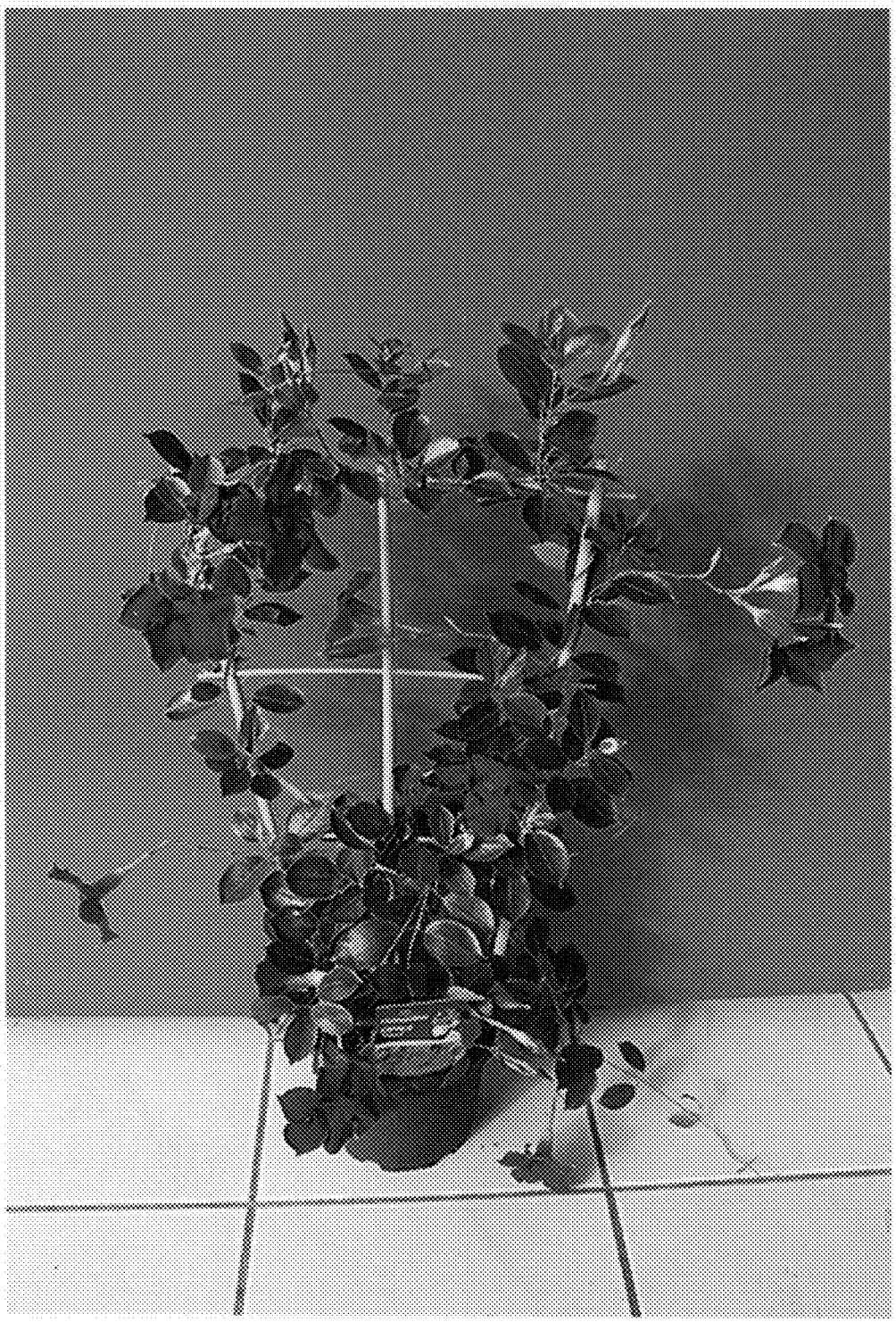

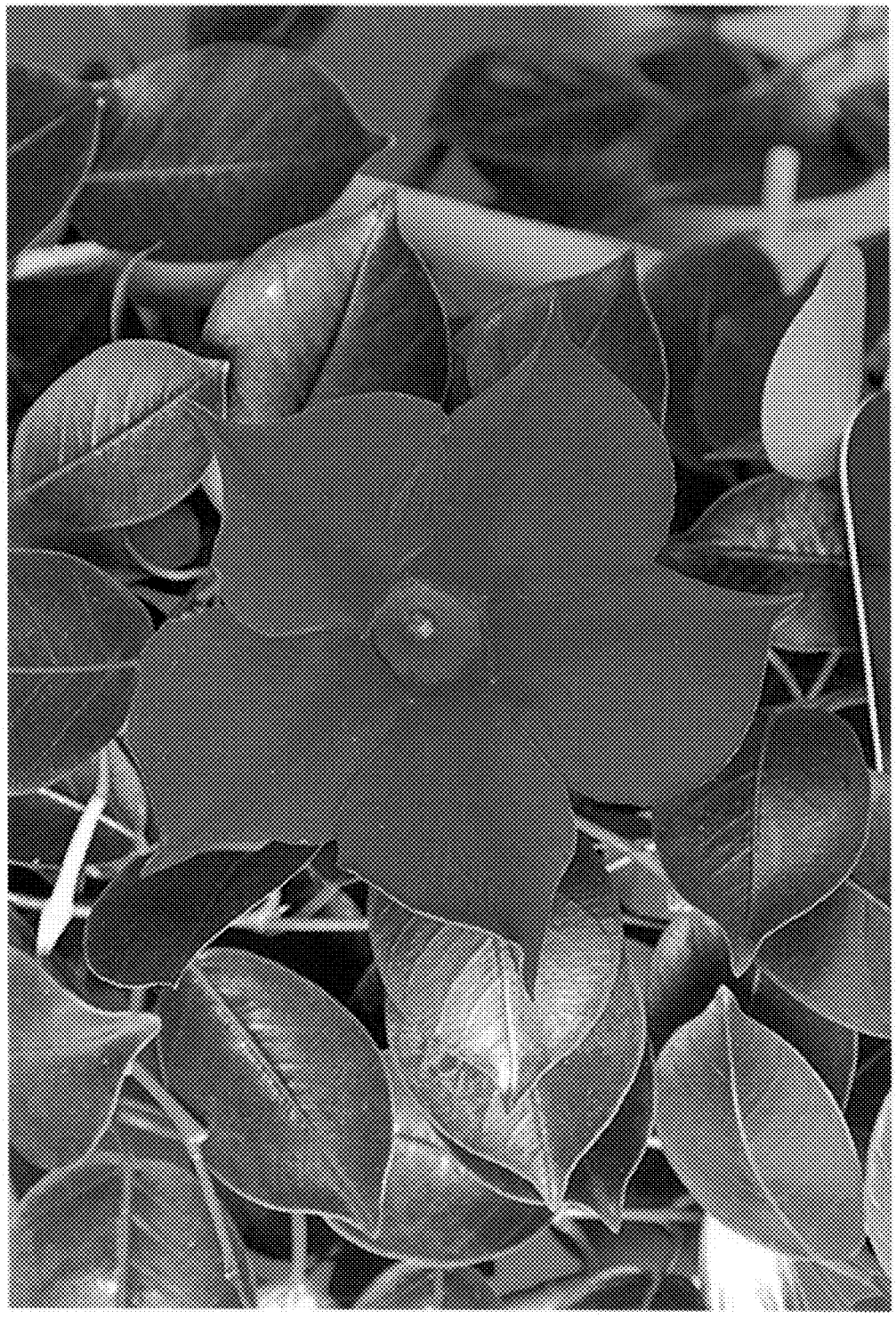

* * * * *